US012053299B2

(12) United States Patent
Saha et al.

(10) Patent No.: US 12,053,299 B2
(45) Date of Patent: Aug. 6, 2024

(54) SECURE PLATFORM FOR POINT-TO-POINT BRAIN SENSING

(71) Applicant: International Business Machines Corporation, Armonk, NY (US)

(72) Inventors: Amrita Saha, Bangalore (IN); Srikanth Govindaraj Tamilselvam, Bangalore (IN); Pankaj S. Dayama, Bangalore (IN); Priyanka Agrawal, Bangalore (IN)

(73) Assignee: International Business Machines Corporation, Armonk, NY (US)

( * ) Notice: Subject to any disclaimer, the term of this patent is extended or adjusted under 35 U.S.C. 154(b) by 1425 days.

(21) Appl. No.: 16/275,819

(22) Filed: Feb. 14, 2019

(65) Prior Publication Data
US 2020/0261018 A1  Aug. 20, 2020

(51) Int. Cl.
| | |
|---|---|
| *G09B 7/08* | (2006.01) |
| *A61B 5/00* | (2006.01) |
| *A61B 5/16* | (2006.01) |
| *A61B 5/378* | (2021.01) |
| *A61B 5/38* | (2021.01) |
| *G09B 7/04* | (2006.01) |

(52) U.S. Cl.
CPC .............. *A61B 5/486* (2013.01); *A61B 5/165* (2013.01); *A61B 5/378* (2021.01); *A61B 5/38* (2021.01); *A61B 5/7264* (2013.01); *G09B 7/04* (2013.01); *G09B 7/08* (2013.01)

(58) Field of Classification Search
CPC . G09B 5/065; G09B 7/02; G09B 7/04; G09B 7/08
See application file for complete search history.

(56) References Cited

U.S. PATENT DOCUMENTS

| | | | | |
|---|---|---|---|---|
| 4,332,566 A | * | 6/1982 | Mazeski | G09B 17/003 600/545 |
| 5,213,338 A | * | 5/1993 | Brotz | A63F 13/212 434/237 |

(Continued)

FOREIGN PATENT DOCUMENTS

CN       104573359 A       4/2015

OTHER PUBLICATIONS

Yuqiao Gu et al. Using Brain Data for Sentiment Analysis, JLCL 2014—Band 29 (1)—79-94.

(Continued)

*Primary Examiner* — Eddy Saint-Vil
(74) *Attorney, Agent, or Firm* — Ryan, Mason & Lewis, LLP

(57) ABSTRACT

Methods, apparatus, and processor-readable storage media for facilitating a secure platform for point-to-point brain sensing are provided herein. An exemplary method includes presenting a user of a brain-computer interface with learning content; monitoring brain signals of the user using a brain-computer interface while the learning content is being presented; determining, based at least in part on said monitoring, that a confusion state of the user exceeds a personalized confusion threshold in regard to at least a part of the learning content; in response to said determining, outputting information to assist the user in understanding the part of the learning content until the confusion state of the user is below the personalized confusion threshold.

20 Claims, 8 Drawing Sheets

(56) References Cited

U.S. PATENT DOCUMENTS

| | | | | |
|---|---|---|---|---|
| 5,304,112 | A * | 4/1994 | Mrklas | A61M 21/0094 600/27 |
| 5,692,517 | A * | 12/1997 | Junker | A61B 5/375 345/157 |
| 5,911,581 | A * | 6/1999 | Reynolds | G09B 7/04 434/236 |
| 6,155,974 | A * | 12/2000 | Fish | A61B 5/0006 128/903 |
| 6,402,520 | B1 * | 6/2002 | Freer | G09B 19/00 434/362 |
| 6,450,820 | B1 * | 9/2002 | Palsson | G09B 19/22 434/238 |
| 6,546,378 | B1 * | 4/2003 | Cook | A61B 5/316 706/20 |
| 7,076,736 | B2 | 7/2006 | Hugh | |
| 8,560,100 | B2 * | 10/2013 | Sarkis | G09B 19/00 434/319 |
| 9,042,201 | B2 | 5/2015 | Tyler et al. | |
| 9,451,899 | B2 | 9/2016 | Ritchey et al. | |
| 9,594,944 | B2 | 3/2017 | Kompalli et al. | |
| 9,665,551 | B2 | 5/2017 | Zhuang et al. | |
| 9,881,512 | B2 | 1/2018 | Jeyahandarajan | |
| 2003/0059750 | A1 | 3/2003 | Bindler | G09B 23/28 434/236 |
| 2008/0275358 | A1 * | 11/2008 | Freer | G09B 7/02 434/236 |
| 2010/0009324 | A1 * | 1/2010 | Owens | G09B 23/28 434/236 |
| 2012/0156667 | A1 * | 6/2012 | Singer | G09B 5/00 434/350 |
| 2013/0006717 | A1 | 1/2013 | Oleson et al. | |
| 2013/0144937 | A1 * | 6/2013 | Lee | G06N 7/023 709/224 |
| 2013/0260361 | A1 * | 10/2013 | Mutlu | G09B 19/00 434/365 |
| 2014/0200432 | A1 * | 7/2014 | Banerji | G09B 19/003 607/54 |
| 2014/0335489 | A1 * | 11/2014 | DeCharms | G09B 19/00 434/236 |
| 2016/0082319 | A1 * | 3/2016 | Macri | G09B 19/003 434/257 |
| 2016/0180722 | A1 * | 6/2016 | Yehezkel | G09B 5/00 434/236 |
| 2017/0186331 | A1 | 1/2017 | Lawrenson et al. | |
| 2017/0085547 | A1 | 3/2017 | De Aguiar et al. | |
| 2017/0315825 | A1 | 11/2017 | Gordon et al. | |
| 2018/0018540 | A1 * | 1/2018 | Hazur | G09B 5/065 |
| 2018/0286272 | A1 * | 10/2018 | McDermott | G09B 5/06 |

OTHER PUBLICATIONS

Taciana Saad Rached et al. Emotion Recognition Based on Brain-Computer Interface Systems, Open Access Peer-Reviewed Chapter, Jun. 5, 2013, DOI: 10.5772/56227.

Lee Y-Y, Hsieh S (2014) Classifying Different Emotional States by Means of EEG-Based Functional Connectivity Patterns. PLoS ONE 9(4): e95415. doi: 10.1371/journal.pone.0095415.

Robin Tibor Schirrmeister et al. Deep Learning with Convolutional Neural Networks for EEG Decoding and Visualization, Human Brain Mapping 38:5391-5420 (2017).

Allan Ajifo, Direct Brain-to-Brain Communication Used in Humans, IFL Science, 2019.

Kurzweilaccelerating Intelligence Digest, First Brain-to-Brain 'Telepathy' Communication via the Internet, Sep. 24, 2015.

Grau C, Ginhoux R, Riera A, Nguyen TL, Chauvat H, et al. (2014) Conscious Brain-to-Brain Communication in Humans Using Non-Invasive Technologies. PLoS ONE 9(8): e105225. doi:10.1371/journal.pone.0105225.

Amy Adams, Brain-Sensing Technology Allows Typing at 12 Words per Minute, Stanford News, Sep. 12, 2016.

Honglei Zhuang et al. Leveraging In-Batch Annotation Bias for Crowdsourced Active Learning, WSDM'15, Feb. 2-6, 2015.

Kiang Zhang et al. Converting Your Thoughts to Texts: Enabling Brain Typing via Deep Feature Learning of EEG Signals, ResearchGate, Conference Paper, Mar. 2018, DOI: 10.1109/PERCOM.2018.8444575.

Ahmed Ben Said et al, "Multimodal deep learning approach for joint EEG-EMG data compression and classification," (May 27, 2017).

Md. Khayrul Bashar, "ECG and EEG Based Multimodal Biometrics for Human Identification," 2018 IEEE International Conference on Systems, Man, and Cybernetics (Dec. 31, 2018).

* cited by examiner

SECURE PLATFORM FOR POINT-TO-POINT BRAIN SENSING

FIELD

The present application generally relates to information technology and, more particularly, to brain signal analysis.

BACKGROUND

Brainwaves are produced by synchronized electrical pulses from masses of neurons communicating with each other. Recent technological advances have enabled non-invasive sensors to read these brain signals and map them to, for example, words and emotions.

SUMMARY

In one embodiment of the present invention, techniques for facilitating a secure platform for point-to-point brain sensing are provided. An exemplary computer-implemented method can include a step of presenting a user of a brain-computer interface with learning content. The method also includes a step of monitoring brain signals of the user using a brain-computer interface while the learning content is being presented. The method further includes a step of determining, based at least in part on said monitoring, that a confusion state of the user exceeds a personalized confusion threshold in regard to at least a part of the learning content. Additionally, the method includes a step of, in response to said determining, outputting information to assist the user in understanding the part of the learning content until the confusion state of the user is below the personalized confusion threshold.

Another exemplary computer-implemented method includes continuously monitoring (i) brain signals of a user of a brain-computer interface and (ii) multimodal data related to an environment of the user. Such a method also includes generating, based at least in part on said monitoring, at least one unique mapping between (i) the brain signals of the user and (ii) generic multimodal representations corresponding to the environment of the user. Further, such a method additionally includes storing a first set of brain signals of the user at least by (i) encoding the first set of brain signals to a first set of generic multimodal representations based at least in part on the at least one unique mapping of the user and (ii) storing the first set of generic multimodal representations in at least one memory.

Another embodiment of the invention or elements thereof can be implemented in the form of a computer program product tangibly embodying computer readable instructions which, when implemented, cause a computer to carry out a plurality of method steps, as described herein. Furthermore, another embodiment of the invention or elements thereof can be implemented in the form of a system including a memory and at least one processor that is coupled to the memory and configured to perform noted method steps. Yet further, another embodiment of the invention or elements thereof can be implemented in the form of means for carrying out the method steps described herein, or elements thereof; the means can include hardware module(s) or a combination of hardware and software modules, wherein the software modules are stored in a tangible computer-readable storage medium (or multiple such media).

These and other objects, features and advantages of the present invention will become apparent from the following detailed description of illustrative embodiments thereof, which is to be read in connection with the accompanying drawings.

DETAILED DESCRIPTION

Advancements in brain sensing technologies open new possibilities, such as direct brain-to-brain communications between users, for example. Such advancements also present new challenges related to such communication including, for instance, the security of the communication, learning personalized brain signal mappings, and filtering of brain signals for one or more particular events. To facilitate deeper cognitive functions, there is a need for brain sensing platforms to support, for example, compliant brain signals data storage, Common-Contextual Representation Learning (CCRL), disambiguation of confused intent from CCRL, applications for use cases where current artificial intelligence solutions are not suitable (such as for gaze and multi-modal signals), etc.

Various exemplary embodiments herein describe techniques for facilitating secure platforms for point-to-point brain sensing.

Figure 1:
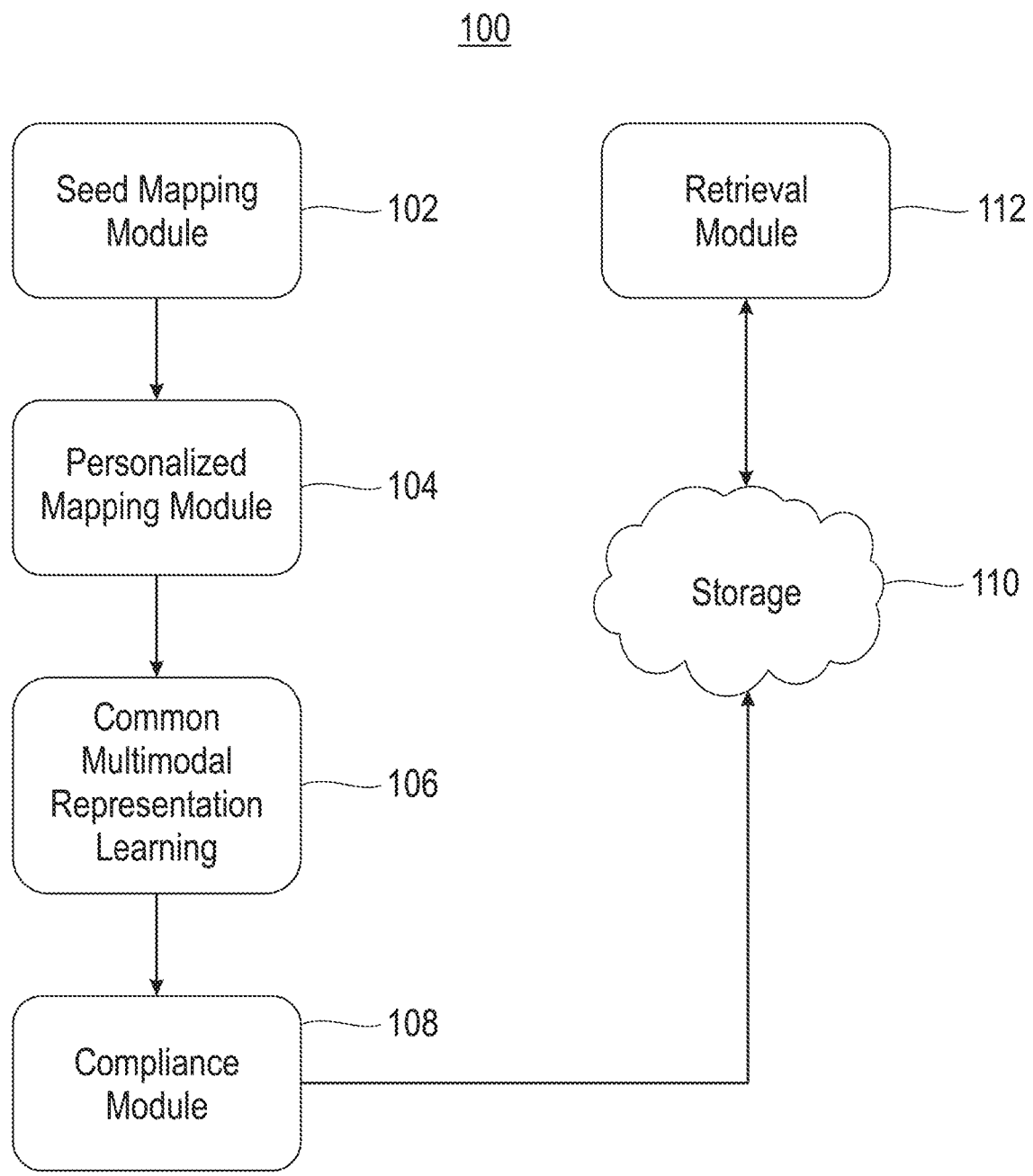
FIG. 1 is a diagram illustrating system architecture, according to an exemplary embodiment of the invention.

Referring now to FIG. 1, this figure is a simplified block diagram of a system architecture 100 for securely storing and retrieving brain signal data in accordance with various example embodiments. By way of illustration, FIG. 1 depicts a seed mapping module 102, a personalized mapping module 104, a common multimodal representation learning module 106, compliance module 108, storage 110 (such as cloud storage, for example), and a retrieval module 112.

The seed mapping module 102 obtains mappings for particular groups of users, such as, for example, for age groups and/or other characteristics. The seed mapping module 102 maps brain signals to different kinds of external stimuli that generate patterns of signals in the brain. These external stimuli may cause an individual to think of a specific word (such as an action keyword or object, for example), or be associated with an individual's specific mental state (such as attentiveness, confusion, sentiment and emotion, for example). The initial seed mapping module 102 can obtain various mappings for the particular groups of users, which may include one or more of the following:

Brainwave signals and action keywords;

Brainwave signals and noun keywords;
Brainwave signals and an attentivity map;
Brainwave signals and a confusion map;
Brainwave signals and a sentiment map; and
Brainwave signals and an emotion map.

The mapping functions obtained by the seed mapping module 102 are clustered across the particular groups. For example, groups may be clustered according to age ranges of the users, other characteristics of the users, and/or the like. It is noted that some of these mappings may form more well-defined clusters, while other mapping functions are more personalized and thus less well-defined. As an example, mappings that are more well-defined are generally more generic and consistent across users, such as a mapping between brain-signals and an attentivity state and a mapping between brain-signals and a confusion state; whereas the mapping between brain-signals and word(s) is generally more personalized. The correct cluster is identified based on the user's age/characteristics information.

The personalized mapping module 104 builds personalized mappings between brain signal representations and words, images, sounds, and/or other modalities. In some example embodiments, the personalized mapping module 104 includes a supervised learning phase for fine-tuning the mapping between brain-signals and predetermined external stimuli presented to the user. Alternatively, or additionally, contextual information may be automatically gathered in different modalities without explicit engagement from the user, such as via Internet of Things (IoT) devices, for example. These devices may include devices that measure and/or track a user's mental state based on external manifestation in the user's biometrics, such as dilation of a user's pupils, measurements of the user's heartbeat, and/or other biometrics.

The user's brain signals are continuously monitored using a brain-computer interface (e.g., any suitable device that senses activity, such as electrical activity, in the user's brain) for changes in the brain signals based on external stimuli. The seed mapping may be continuously tuned over time (e.g., via machine learning) based on the user's data (such as data from TOT devices and data of the user's brain signals, for example).

The common multimodal representation learning module 106 maximizes the correlation between brainwave signals and contextual information (such as sound, video, image, hologram, text, and/or other modalities) to determine a common multimodal representation (also referred to herein as a 'generic' multimodal representation). Because a user's brain signals may be stored remotely in storage (such as in cloud storage 110, for example), the compliance module 108 acts as a privacy filter for the brain signals such that only brain signals related to a particular event are stored in order not to infringe on the user's privacy. For example, if a user is taking an open textbook test, the compliance module 108 may ensure that the only brain signals relevant to the prescribed textbook are stored (or retrieved). Based on the learnt mapping between the brain signals and mappings (such as mappings between brain signals and action keywords, brain signals and noun keywords, etc.), only the compliant brain signals are stored in storage 110 in the common multimodal representation form.

Figure 2:
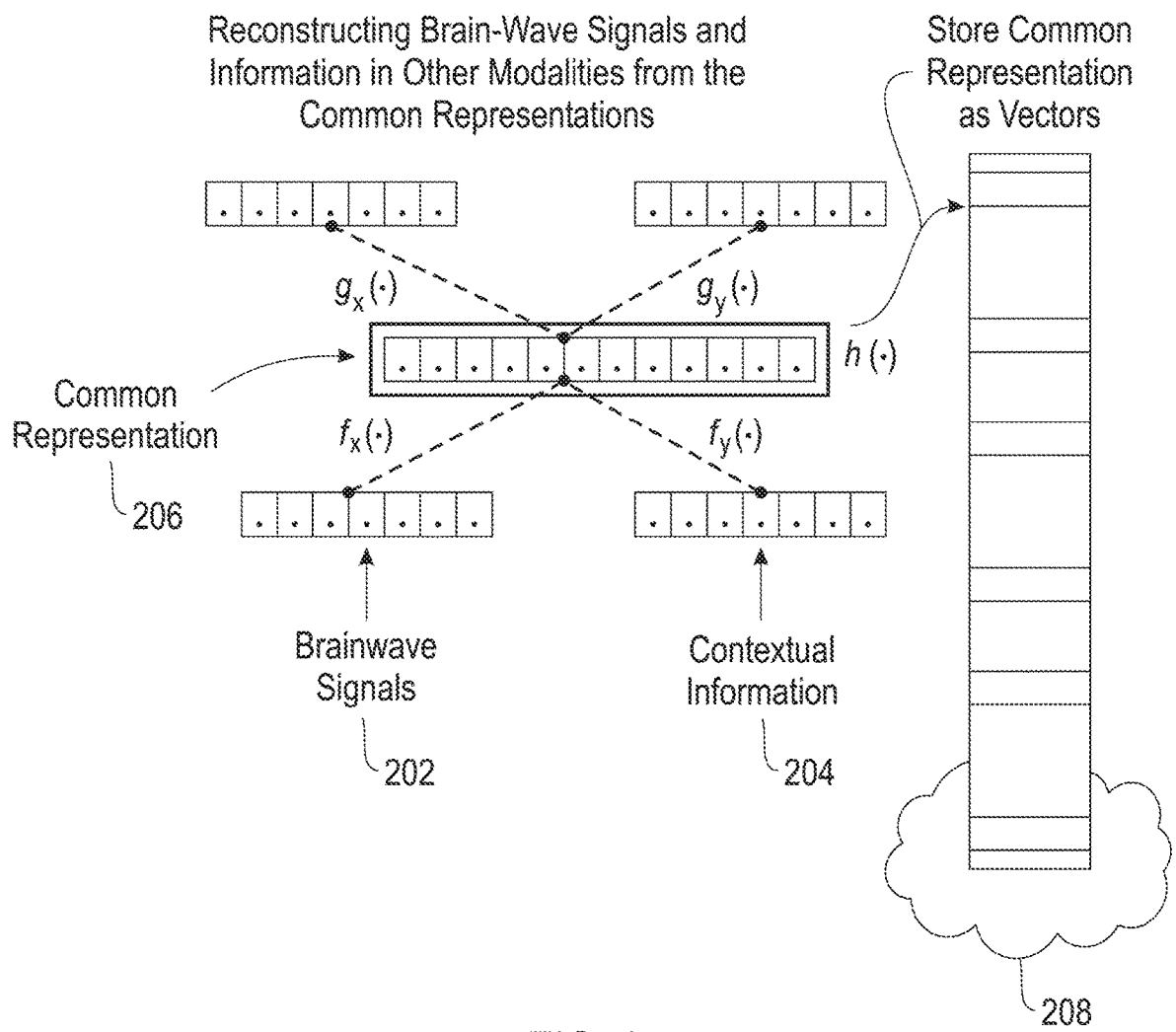
FIG. 2 is a diagram illustrating an example flow diagram for storing common multimodal representations in accordance with an example embodiment of the invention.

Referring now to FIG. 2, this figure shows an example flow diagram for storing common multimodal representations in accordance with an example embodiment. In the example shown in FIG. 2, there is a mapping between brainwave signals 202 and contextual information 204 for particular modality (such as an image, for example) to form a common multimodal representation 206. Brainwave signals and information in other modalities may then be reconstructed from the common multimodal representation 206. The common multimodal representation is stored in storage 208, which in this example is a cloud store. According to some example embodiments, the common multimodal representations of past thoughts may then be stored as vectors using a nearest neighbor (NN) index in the storage.

Figure 3:
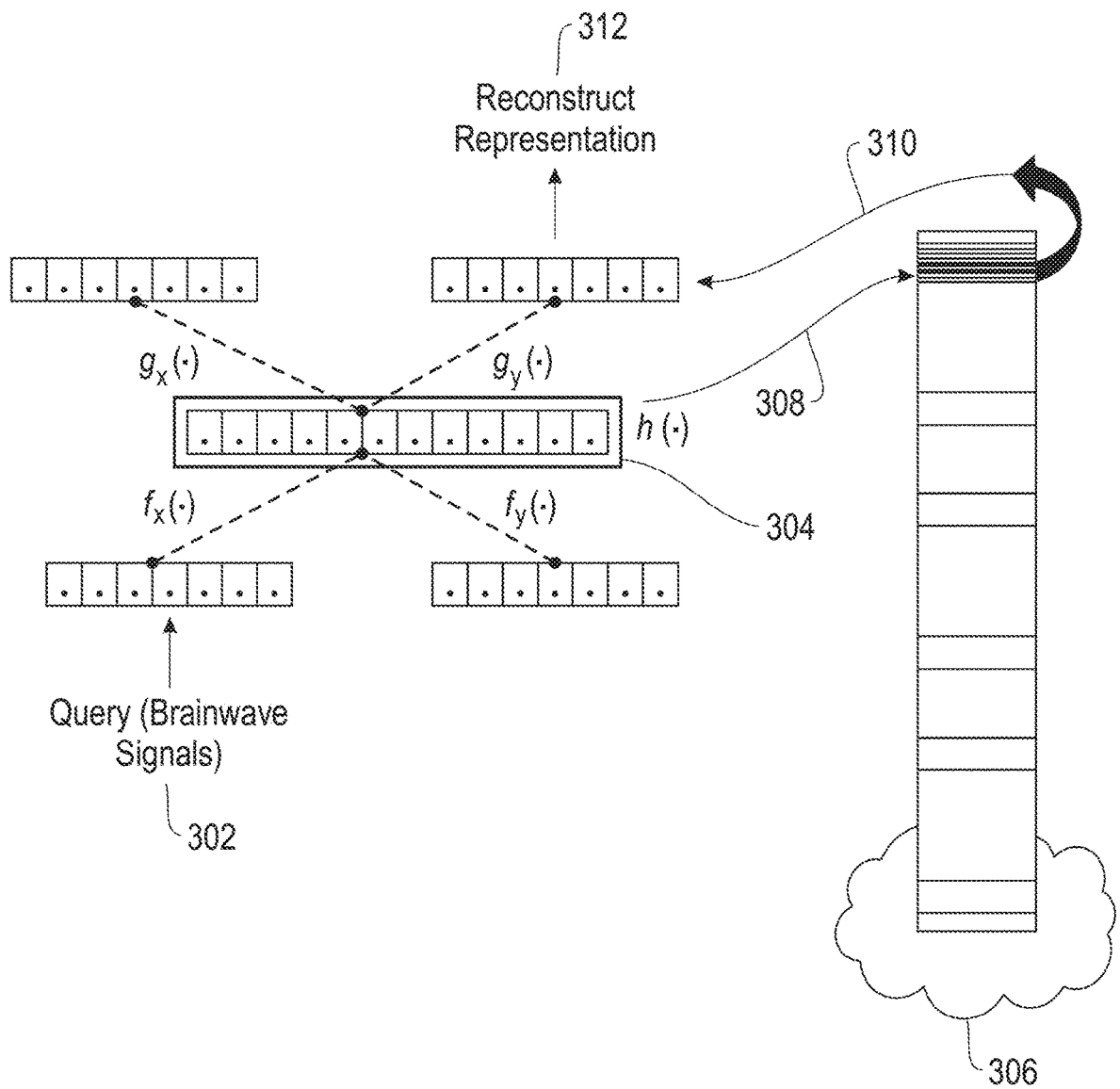
FIG. 3 is a diagram illustrating an example flow diagram for retrieving a stored common multimodal representation in accordance with an example embodiment of the invention.

FIG. 3 shows an example flow diagram for retrieving a stored common multimodal representation in accordance with an example embodiment. According to some example embodiments, the flow diagram in FIG. 3 corresponds to the retrieval module 112. In FIG. 3, the user generates a context query 302 in the form of a set of brain signals. The context query 302 is mapped to a common multimodal representation form 304, which is used to lookup (via action 308) the closest stored common multimodal representations (corresponding to previous brain signals of the user) relevant in the current context in storage 306. The lookup 308 is performed using an NN-index, for example. In response, the closest common multimodal representations that are stored in the cloud store 306 are returned in step 310. The returned common multimodal representation may then be used to reconstruct a contextual representation 312 via one or more modalities.

Referring again to FIG. 1, according to some example embodiments, the retrieval module 112 may also utilize confusion signals determined in the user's brainwaves over time to perform a personalized relevance ranking of results returned from the lookup. Confusion signals relate to a user's confusion state for some external stimuli. As such, the results may be ranked such that results expected to be less confusing will be ranked higher. According to at least one embodiment, the confusion signals are read in brainwaves over time to learn the user's preferred modality of visualizing particular thoughts. Thus, in some example embodiments, the retrieval module 112 decodes the common multimodal representation using this determined preferred modality.

Figure 4:
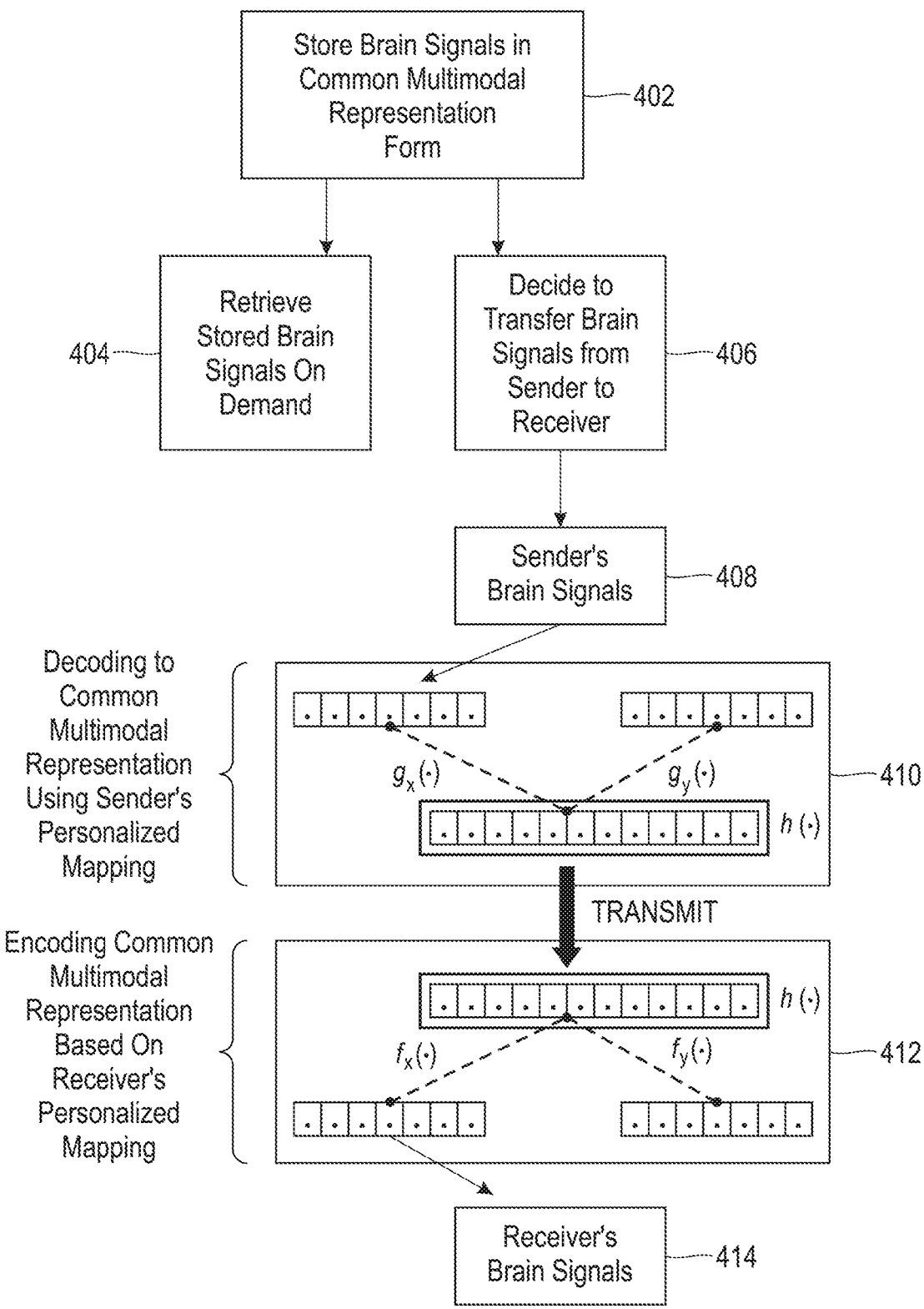
FIG. 4 is a simplified flow diagram for a brain-to-brain communication system in accordance with an example embodiment of the invention.

Referring now to FIG. 4, this figure shows a simplified flow diagram for a brain-to-brain communication system in accordance with various example embodiments. At block 402, a user stores brain signals in the common multimodal representation form (such as described above with reference to FIG. 2, for example).

At block 404, the user may retrieve the stored brain signals on demand by decoding the previously-stored common multimodal representations with the user's personalized mapping. Each of these common multimodal representations may be shown to the user using the most appropriate modality. In other cases, the user may decide to transfer his or her current brain signal remotely to another user as shown at block 406. In these cases, the user's brain signals 408 are decoded (via action 410) to the common multimodal representation using the user's personalized mapping, and are transmitted to the receiving user. The transmitted common multimodal representation is then encoded (via action 412) to the receiving user's brain signals 414 based on the receiving user's personalized mapping. It is noted that by using the common representation learning paradigm, the receiving user's device does not have knowledge of the sending user's personalized mapping, and the sending user's device does not have knowledge of the receiver user's personalized mapping.

In some example embodiments, the brain signals communicated between the users may be filtered in a manner similar to that described above with respect to compliance module 108. For instance, the communication may be defined for a specific activity (such as official events or social events, for example). The mapping is learnt only for the kind of brain signals to which the user has given consent. For non-compliant brain signals, the mapping will give a meaningless representation in the common multimodal latent space, such as by performing a random mapping on the non-compliant brain signals. Only the compliant brain signals are decoded to the common multimodal representation and transferred to the receiving user's brain-computer interface device (such as an EEG device, for example).

It is to be appreciated that applications related to various example embodiments are particularly helpful in learning and/or therapeutic environments. For example, some example embodiments are relevant to one or more of: multi-concept disambiguation, improved insight into educational and/or therapeutic techniques, and unbiased crowdsourcing, for example.

For example, a brain sensing platform (such as system architecture 100) may include tracking a first user's emotions, based on the first user's brain signals, while the first user is writing a social media post. The brain sensing platform may also track a second user's confusion signals while the second user is reading the social media post. For example, assume the first user is an Indian in his 20s, and that the second user is a native of the United States and also in his 20s. The first user may publish a social media post that references an 'auto-driver,' wherein the emotion of the first user behind the post includes sarcasm, frustration, and humor. When the second user reads the post, the brain sensing platform detects confusion from the second user's brain signals, and looks up the second user's memory store for the concept 'auto-driver.' According to some example embodiments, other sources of information may also be used (such as the Internet) in addition to the second user's memory store. If the brain sensing platform still detects that the second user's confusion is above his personalized confusion threshold (PCT), then the search may be expanded to the memory storage of other users having different characteristics to fetch emotions associated with the concept 'auto-driver' for all users of a particular group when the first user was posting on that subject. In some examples, the PCT is determined for each specific user in the initial phase (i.e., the training phase) by learning what threshold is best for that specific user for a specific task. The brain sensing platform may gather more context from the first user by retrieving 'auto-driver' related information in the first user's past which had aroused similar emotions (such as anecdotes, for example), and presenting such information to the second user. This information may then be used to determine that the best modality for the second user is through anecdotes. At this point, the brain sensing platform determines that the second user's confusion is reduced below his PCT after providing this additional information.

It is noted that in some example embodiments, the brain sensing platform may only need to track, store and retrieve the emotional responses of different users having different characteristics when consuming information about different concepts.

In another non-limiting example, a brain sensing platform (such as system architecture 100) may include guiding a user to understand some particular concept by tracking a confusion state of the user over time. For example, assume a user in his 20s, is a native of the United States, and is not aware of the Indian delicacy 'rasogolla.' The user comes across an image of rasogolla while reading. In this situation, the brain sensing platform tracks that the user is in a confused state (via, for example, confusion signals). The brain sensing platform encodes the brain signals corresponding to the image into the common multimodal representation based on the user's learnt personalized mapping, and fetches concepts familiar to the user based on the common multimodal representation (such as images of dumplings, for example). The brain sensing platform tracks that the user's confusion is reduced, but still above his PCT. The brain sensing platform explores the common multimodal representations learnt from users of other backgrounds (e.g., from other countries), and retrieves, for example, more context about rasogolla representations learnt from those other users. It is noted that retrieving this additional context may include performing multiple iterations using various strategies, such as searching for additional context for users within the same region but having different age groups, lifestyle, or using different regions with respect to the same age group, for example. The brain sensing platform then determines the user's confusion is reduced beyond his personalized confusion threshold (PCT) after providing this additional information.

In another non-limiting example, a brain sensing platform (such as system architecture 100) is utilized for multi-concept disambiguation. For example, assume a user has the following attributes:

Demographics: Native of United States
Age-group: 20s;
Culture: Western; and
Interests: Modeling, American Football Also assume the user is not aware that a famous model is also a star football player (i.e., a soccer player). When the user comes across an image of the model playing soccer with a caption "football star," the brain sensing platform may determine that the user is currently in a confused state, namely, because the user's personal common multimodal representation shows him as a 'model' (i.e., based on the user's personalized mapping). The brain sensing platform encodes the image in the common multimodal representation form based on the users' personal mapping, and uses the memory store to fetch nearest concepts familiar to the user, such as modeling images that include the player. The brain sensing platform tracks that the user is still confused above his PCT due to the confusions over the term 'football' and American football. The brain sensing platform fetches common multimodal representations learnt from users having other characteristics. For example, the brain sensing platform retrieves more context about the player from common multimodal representations learnt from European users, which help the user understand that the term 'football' refers to soccer as opposed to American football. The brain sensing platform determines the user's confusion is reduced beyond his PCT after providing this additional information.

According to some example embodiments, a user's brain signals may be tracked while performing some activity (such as while performing a homework assignment, for example), and certain brain signals may be mapped to at least part of the activity (e.g., at least a part of a particular problem, answer, etc.) and be stored in the common multimodal representation form (such as by utilizing system architecture 100). In such cases, the user may define which emotions are to be shared.

According to at least one example embodiment, a system for a brain-computer interface is provided for unbiased crowdsourcing using differential annotator analysis. As an example, the system may monitor brain signals of a group of annotators and create brain logs comprising brain signals of the respective annotators in the group. These brain signals may be monitored and stored in a similar manner as described above with respect to system architecture 100. The system may then determine relative confidence values for annotations performed by a specific annotator by performing a differential analysis across the brain logs of all of the annotators. In some example embodiments, the system intervenes when an annotator's personalized confusion threshold is above a given threshold, and thus may maximize annotator output or provide the annotator a suitable task.

Consider an example scenario wherein two users are given a task to read some text and then label whether paragraphs are accurate paraphrases of the text. Assume that the text relates to finance, and that the first user is a finance expert and the second user is unfamiliar with finance concepts. In this example, the system monitors the first user's brain signals and determines that the first user was confident in labeling these paragraphs correctly. The system monitors the brainwaves of the second user and determines that the user is in a confused state that is above the user's personalized confusion threshold. For example, the second user may be confused about a specific finance term in the text. The system fetches emotions of the first user that are associated with the same specific finance term when the first user was labeling the same paragraphs. The system may then gather more context from the second user, such as by retrieving information (e.g., stored brain signals) about other tasks the second user has performed, such as tasks when the second user felt emotions similar to those felt by the first user when labeling the paragraphs. The system may then provide more suitable tasks for the second user, thus reducing the labeling cost. The system may then track that the second user's confusion is reduced below the second user's personalized confusion threshold when the second user is provided with the more relevant tasks.

It is noted that such annotators are typically evaluated based on active learning methods, annotation comparison, and are limited to, e.g., gaze tracking, time spent and some latent signals, whereas example embodiments allow the system to capture reasoning behind annotations automatically.

Some example embodiments may be utilized for detecting levels of engagement in certain activities (such as for students, for instance). Typically, techniques for analyzing student thought process involves manual inspection (such as retracing a student's steps through a provided procedure), and the use of software (e.g., detecting student comfort on a subject based on student's browsing behavior or online questionnaire, and identifying possibilities on why a mistake could have happened based on gaze, cursor behavior, forums, logs, intermediate test steps, intermediate answers, loaded logical steps, etc.). However, these processes are unable to accurately estimate a student's engagement.

According to at least one example embodiment, techniques are provided for detecting a level of engagement. In some example embodiments, a correct step may be automatically suggested to a user based on variants found through brain logs of intent and observed action. For example, a student who is learning English as a second language and is presented with an image of a caterpillar may be asked to identify the correct spelling of caterpillar from different choices on a computer screen. In this example, the brain sensing system tracks that the user is, e.g., confused and understands that the question is difficult for a student who is still learning English, and thus requires more attention. The cursor movement of the student may be captured, such that if the student hovers around the wrong answer, and the system may alert the user. The student then rectifies, and chooses the correct answer. In some examples, the system provides feedback on how the difficulty of questions among students is calculated or how particular students should be clustered based on, for example, confusion analysis, answers provided by the student, and time taken.

An example of a process according to at least one embodiment for facilitating a secure platform for point-to-point brain sensing includes a step of continuously monitoring (i) brain signals of a user of a brain-computer interface and (ii) multimodal data related to an environment of the user. The process also includes a step of generating, based at least in part on said monitoring, at least one unique mapping between (i) the brain signals of the user and (ii) generic multimodal representations corresponding to the environment of the user. Additionally, the process includes storing a first set of brain signals of the user at least by (i) encoding the first set of brain signals to a first set of generic multimodal representations based at least in part on the at least one unique mapping of the user and (ii) storing the first set of generic multimodal representations in at least one memory.

Each of the generic multimodal representations may represent at least one of: (i) a sound, (ii) a video, (iii) an image, (iv) a hologram, and (v) text. The storing may include filtering the first set of brain signals based on one or more events such that each brain signal in the filtered first set is associated with the one or more events. The storing may include randomly encoding brain signals not associated with the one or more events. The first set of generic multimodal representations may be stored as one or more vectors using a nearest neighbor index. The process may also include a step of generating a context query based at least in part on a second set of brain signals of the user; encoding at least some of the second set of brain signals to a second set of generic multimodal representations based on the at least one unique mapping of the first user; retrieving one or more previously stored generic multimodal representations, wherein the one or more previously stored generic multimodal representations have a semantic similarity that is closest to the second set of generic multimodal representations; and reconstructing brain signals of the user corresponding to the one or more previously stored generic multimodal representations based at least in part on the at least one unique mapping of the user.

Additionally, the process may include monitoring a confusion state of the user over a period time based at least in part on said monitoring the brain signals of the user. The process may also include ranking the retrieved one or more previously stored generic multimodal representations based at least in part on the confusion state of the user. Further, the process may include determining a preferred modality of the user based at least in part on said monitoring the confusion state of the user, wherein said reconstructing comprises using the preferred modality to reconstruct the brain signals of the user. The process may additionally include encoding a second set of brain signals to a second set of generic multimodal representations based on the at least one unique mapping of the user; and transmitting the second set of generic multimodal representations to a further user of a brain-computer interface.

Also, the process may include receiving a transmission from the further user comprising one or more generic multimodal representations associated with brain signals of the further user; and decoding the received one or more generic multimodal representations based at least in part on the at least one unique mapping of the user. The step of generating at least one unique mapping may be based at least in part on one or more characteristics associated with the first user. The first set of brain signals may include electroencephalogram signals. The monitoring may include receiving the multimodal data from one or more Internet of Things devices. The multimodal data may include at least one of: (i) image data; (ii) sound data; (iii) video data; (iv) hologram data; (v) text data; and (vi) brain signal data.

Figure 5:
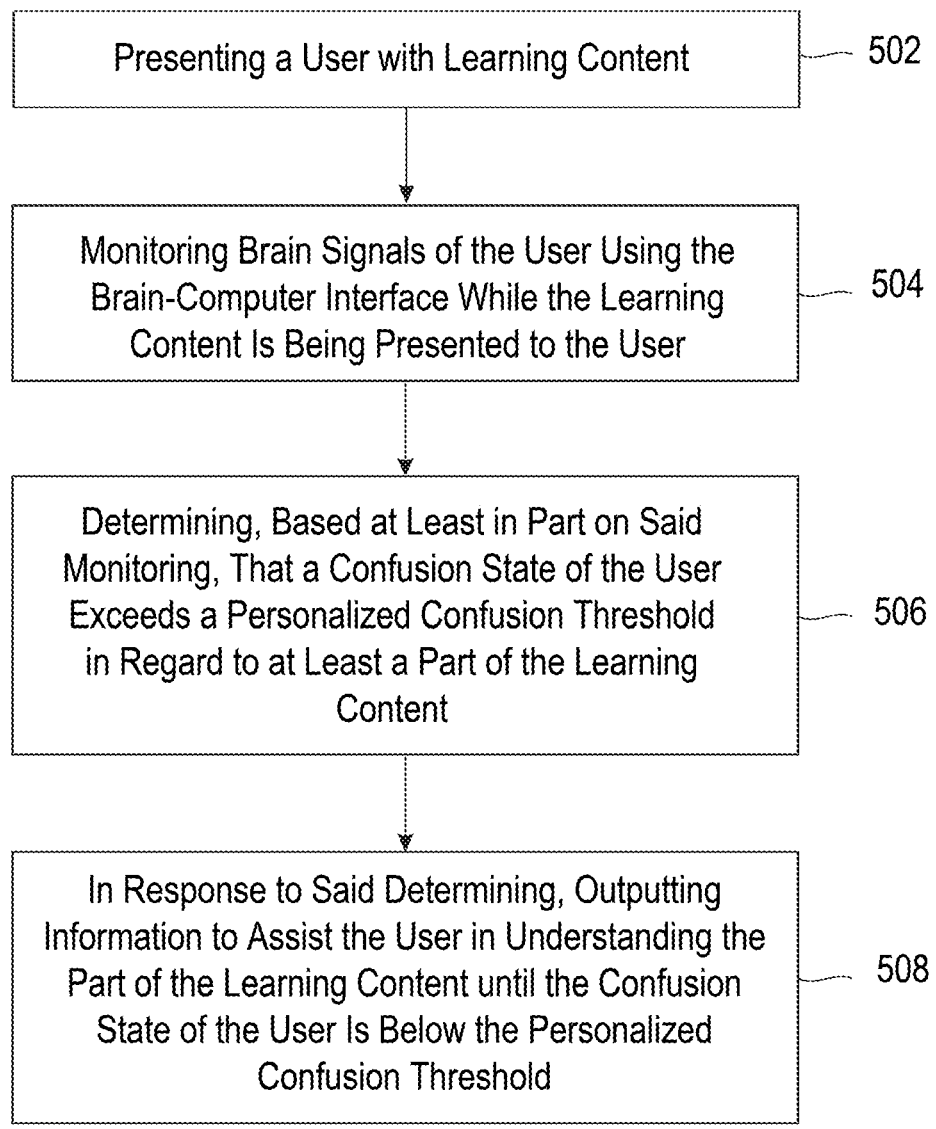
FIG. 5 is a flow diagram illustrating techniques according to an embodiment of the invention.

FIG. 5 is a flow diagram of a process for facilitating a secure platform for point-to-point brain sensing, according to an exemplary embodiment of the invention. Referring to FIG. 5, step 502 of the process includes presenting a user with learning content.

Step 504 of the process includes monitoring brain signals of the user using a brain-computer interface while the learning content is being presented to the user. The monitored brain signals may include electroencephalogram signals.

Step 506 of the process includes determining, based at least in part on said monitoring, that a confusion state of the user exceeds a personalized confusion threshold in regard to at least a part of the learning content. The part of the learning content may include one or more questions, and the outputted information may include information to guide the user to answer the one or more questions correctly. The process may further include determining one or more characteristics associated with the user; and calculating a difficulty level of the question based at least in part on (i) the one or more characteristics associated with the user and (ii) said monitoring.

Step 508 of the process includes, in response to said determining, outputting information to assist the user in understanding the part of the learning content until the confusion state of the user is below the personalized confusion threshold. The outputted information may correspond to at least one of: (i) an image; (ii) a sound; (iii) a video; (iv) a hologram; (v) and (vi) text. Said outputting may include determining a preferred modality of the user based at least in part on said monitoring and said determining. The outputted information comprises further learning content related to one or more related concepts.

According to at least one example embodiment, the process may include generating, using at least one machine learning technique, one or more mappings between (i) previously monitored brain signals of the user and (ii) at least one of: one or more words, one or more images, one or more sounds, and one or more emotions. The confusion threshold may be based at least in part on the one or more mappings.

According to at least one example embodiment, the techniques depicted in FIG. 5 can also include monitoring one or more biometrics of the user using one or more Internet of Things devices, wherein said determining is based at least in part on the monitored one or more biometrics.

The techniques depicted in FIG. 5 can also, as described herein, include providing a system, wherein the system includes distinct software modules, each of the distinct software modules being embodied on a tangible computer-readable recordable storage medium. All of the modules (or any subset thereof) can be on the same medium, or each can be on a different medium, for example. The modules can include any or all of the components shown in the figures and/or described herein. In an embodiment of the invention, the modules can run, for example, on a hardware processor. The method steps can then be carried out using the distinct software modules of the system, as described above, executing on a hardware processor. Further, a computer program product can include a tangible computer-readable recordable storage medium with code adapted to be executed to carry out at least one method step described herein, including the provision of the system with the distinct software modules.

Additionally, the techniques depicted in FIG. 5 can be implemented via a computer program product that can include computer useable program code that is stored in a computer readable storage medium in a data processing system, and wherein the computer useable program code was downloaded over a network from a remote data processing system. Also, in an embodiment of the invention, the computer program product can include computer useable program code that is stored in a computer readable storage medium in a server data processing system, and wherein the computer useable program code is downloaded over a network to a remote data processing system for use in a computer readable storage medium with the remote system.

An embodiment of the invention or elements thereof can be implemented in the form of an apparatus including a memory and at least one processor that is coupled to the memory and configured to perform exemplary method steps.

Figure 6:
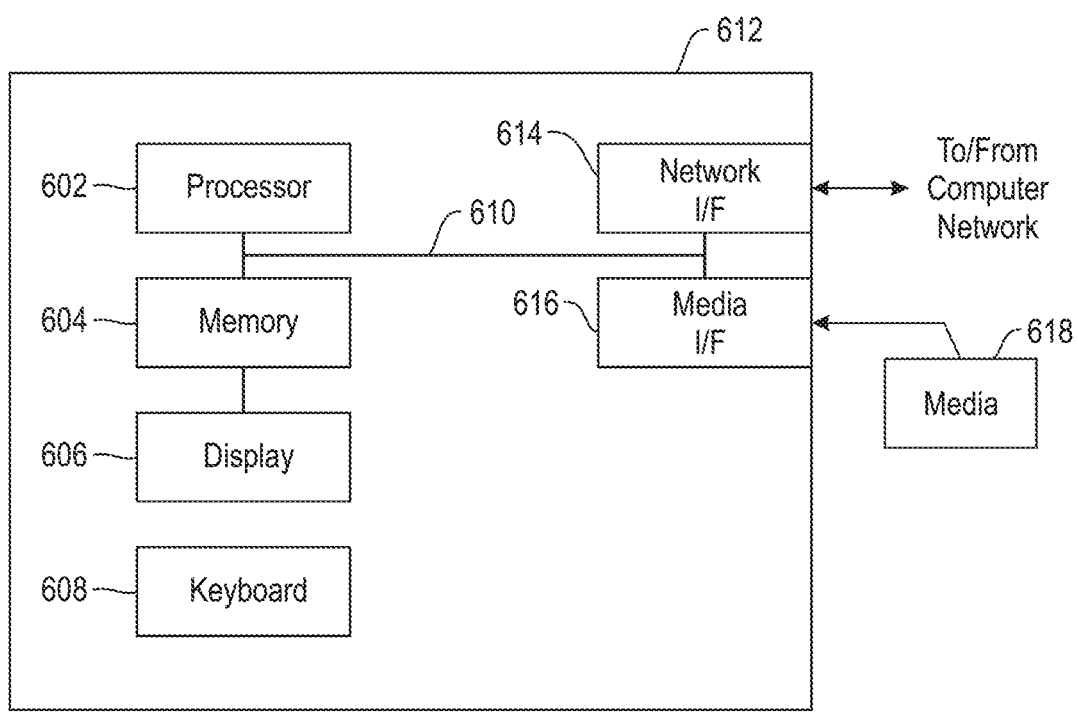
FIG. 6 is a system diagram of an exemplary computer system on which at least one embodiment of the invention can be implemented.

Additionally, an embodiment of the present invention can make use of software running on a computer or workstation. With reference to FIG. 6, such an implementation might employ, for example, a processor 602, a memory 604, and an input/output interface formed, for example, by a display 606 and a keyboard 608. It is noted that in some example embodiments, the The term "processor" as used herein is intended to include any processing device, such as, for example, one that includes a CPU (central processing unit) and/or other forms of processing circuitry. Further, the term "processor" may refer to more than one individual processor. The term "memory" is intended to include memory associated with a processor or CPU, such as, for example, RAM (random access memory), ROM (read only memory), a fixed memory device (for example, hard drive), a removable memory device (for example, diskette), a flash memory and the like. In addition, the phrase "input/output interface" as used herein, is intended to include, for example, a mechanism for inputting data to the processing unit (for example, mouse), and a mechanism for providing results associated with the processing unit (for example, printer). The processor 602, memory 604, and input/output interface such as display 606 and keyboard 608 can be interconnected, for example, via bus 610 as part of a data processing unit 612. Suitable interconnections, for example via bus 610, can also be provided to a network interface 614, such as a network card, which can be provided to interface with a computer network, and to a media interface 616, such as a diskette or CD-ROM drive, which can be provided to interface with media 618.

Accordingly, computer software including instructions or code for performing the methodologies of the invention, as described herein, may be stored in associated memory devices (for example, ROM, fixed or removable memory) and, when ready to be utilized, loaded in part or in whole (for example, into RAM) and implemented by a CPU. Such software could include, but is not limited to, firmware, resident software, microcode, and the like.

A data processing system suitable for storing and/or executing program code will include at least one processor 602 coupled directly or indirectly to memory elements 604 through a system bus 610. The memory elements can include local memory employed during actual implementation of the program code, bulk storage, and cache memories which provide temporary storage of at least some program code in order to reduce the number of times code must be retrieved from bulk storage during implementation.

Input/output or I/O devices (including, but not limited to, keyboards 608, displays 606, pointing devices, brain sensing device and the like) can be coupled to the system either directly (such as via bus 610) or through intervening I/O controllers (omitted for clarity).

Network adapters such as network interface 614 may also be coupled to the system to enable the data processing system to become coupled to other data processing systems or remote printers or storage devices through intervening private or public networks. Modems, cable modems and Ethernet cards are just a few of the currently available types of network adapters.

As used herein, including the claims, a "server" includes a physical data processing system (for example, system 612 as shown in FIG. 6) running a server program. It will be understood that such a physical server may or may not include a display and keyboard.

The present invention may be a system, a method, and/or a computer program product at any possible technical detail level of integration. The computer program product may include a computer readable storage medium (or media) having computer readable program instructions thereon for causing a processor to carry out embodiments of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform embodiments of the present invention.

Embodiments of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

It should be noted that any of the methods described herein can include an additional step of providing a system comprising distinct software modules embodied on a computer readable storage medium; the modules can include, for example, any or all of the components detailed herein. The method steps can then be carried out using the distinct software modules and/or sub-modules of the system, as described above, executing on a hardware processor 602. Further, a computer program product can include a computer-readable storage medium with code adapted to be implemented to carry out at least one method step described herein, including the provision of the system with the distinct software modules.

In any case, it should be understood that the components illustrated herein may be implemented in various forms of hardware, software, or combinations thereof, for example, application specific integrated circuit(s) (ASICS), functional circuitry, an appropriately programmed digital computer with associated memory, and the like. Given the teachings of the invention provided herein, one of ordinary skill in the related art will be able to contemplate other implementations of the components of the invention.

Additionally, it is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (for example, networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as Follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (for example, country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (for example, storage, processing, bandwidth, and active user accounts). Resource usage can be monitored, controlled, and reported providing transparency for both the provider and consumer of the utilized service.

Service Models are as Follows:

Software as a Service (SaaS): the capability provided to the consumer is to use the provider's applications running on a cloud infrastructure. The applications are accessible from various client devices through a thin client interface such as a web browser (for example, web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (for example, host firewalls).

Deployment Models are as Follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (for example, mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (for example, cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 7:
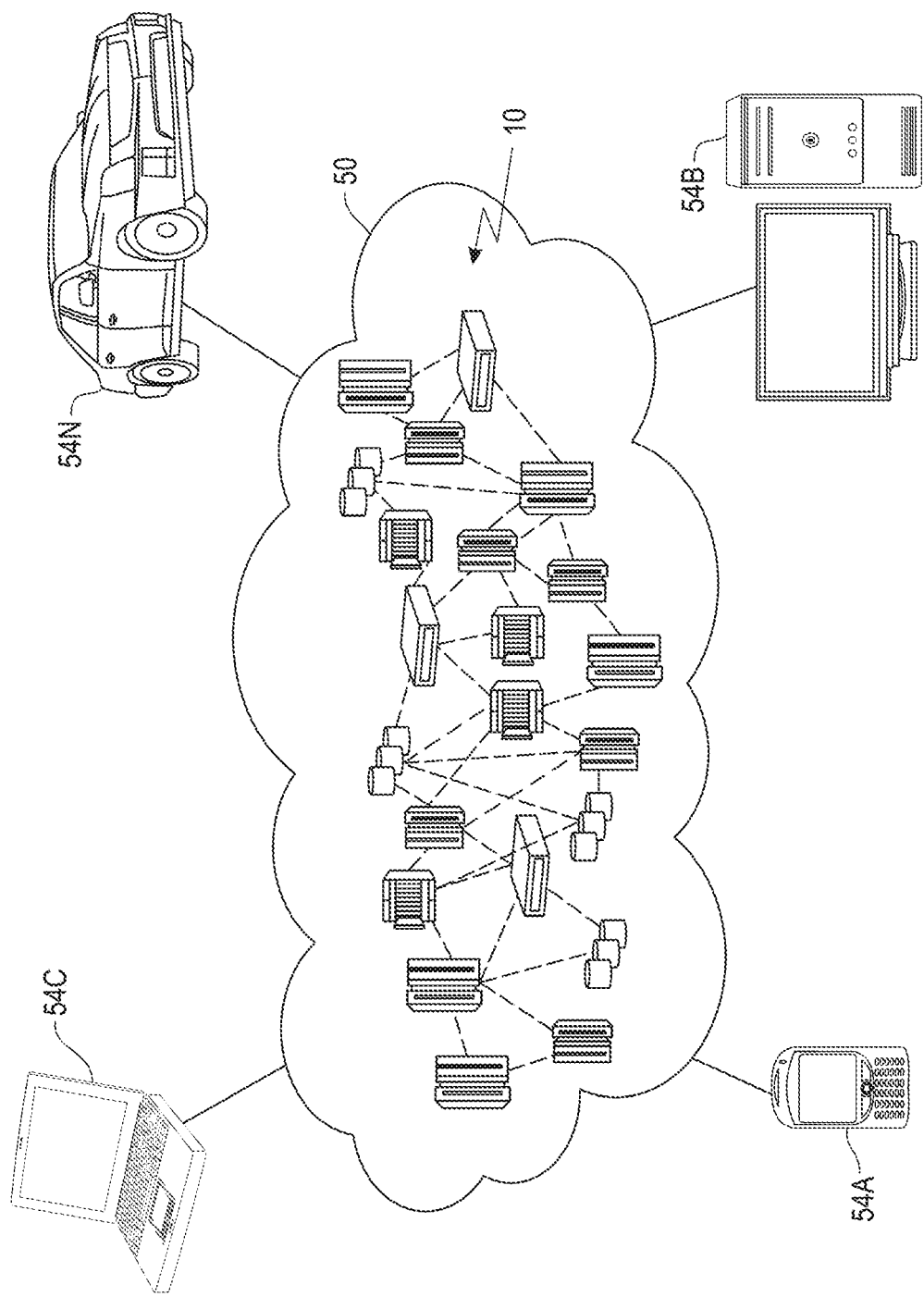
FIG. 7 depicts a cloud computing environment according to an embodiment of the present invention.

Referring now to FIG. 7, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 7 are intended to be illustrative only and that computing nodes 10 and cloud computing environment 50 can communicate with any type of computerized device over any type of network and/or network addressable connection (e.g., using a web browser).

Figure 8:
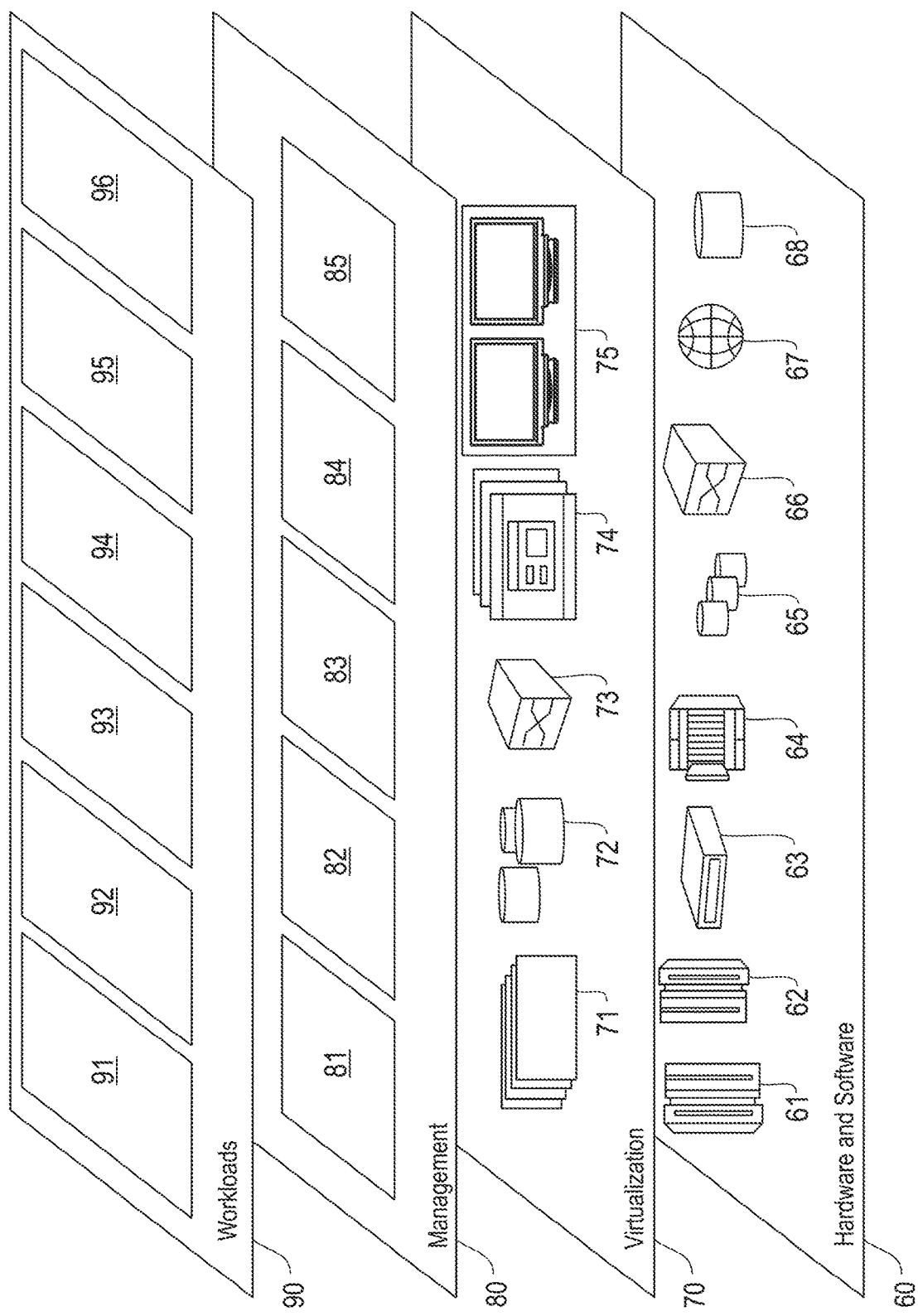
FIG. 8 depicts abstraction model layers according to an embodiment of the present invention.

Referring now to FIG. 8, a set of functional abstraction layers provided by cloud computing environment 50 (FIG. 7) is shown. It should be understood in advance that the components, layers, and functions shown in FIG. 8 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture-based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75. In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources.

In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and secure storage, retrieval and communication of brain signals 96, in accordance with the one or more embodiments of the present invention.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of another feature, step, operation, element, component, and/or group thereof.

At least one embodiment of the present invention may provide a beneficial effect such as, for example, providing a secure system for storing, retrieving, and communicating brain signals. At least one embodiment of the present invention may provide a beneficial effect such as, for example, providing novel input in the form of brain signals to further enhance and/or replace other inputs (e.g., gaze, tactile, and image-based technologies).

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method, the method comprising:
presenting, by at least one processor of a brain sensing computing platform, a user with learning content;
monitoring, by the at least one processor of the brain sensing computing platform, brain signals of the user using a brain-computer interface associated with the brain sensing computing platform while the learning content is being presented to the user;
filtering, by the at least one processor of the brain sensing computing platform, the monitored brain signals to identify brain signals associated with a confusion state of the user, wherein the filtering removes one or more of the monitored brain signals based at least in part on one or more mappings between previously monitored brain signals of the user and one or more emotional states;
encoding, by the at least one processor of the brain sensing computing platform, the identified brain signals associated with the confusion state of the user using a first encoding scheme that is based at least in part on the one or more mappings corresponding to the user;
storing the encoded brain signals in a storage system associated with the brain sensing computing platform;
determining, by the at least one processor of the brain sensing computing platform based at least in part on the encoded brain signals stored in the storage system, that a confusion state of the user exceeds a personalized confusion threshold in regard to at least a part of the learning content; and in response to said determining, outputting, by the at least one processor of the brain sensing computing platform, information to assist the user in understanding the part of the learning content until the confusion state of the user falls below the personalized confusion threshold;

wherein the method is performed by at least one computing device.

2. The computer-implemented method of claim 1, comprising:

generating, using at least one machine learning process, the one or more mappings between previously monitored brain signals of the user, wherein the one or more mappings further comprise at least one mapping between the previously monitored brain signal of the user and at least one of:

one or more words; one or more images; and one or more sounds, and wherein the personalized confusion threshold is based at least in part on the one or more mappings.

3. The computer-implemented method of claim 1, wherein the part of the learning content comprises one or more questions, and wherein the outputted information comprises further learning content related to one or more related concepts to guide the user to answer the one or more questions correctly.

4. The computer-implemented method of claim 3, comprising:

determining one or more characteristics associated with the user; and calculating a difficulty level of the one or more questions based at least in part on the one or more characteristics associated with the user and said monitoring.

5. The computer-implemented method of claim 1, wherein the outputted information corresponds to at least one of: an image; a sound; a video; a hologram; and text, and wherein said outputting comprises determining a preferred modality of the user based at least in part on said monitoring and said determining.

6. The computer-implemented method of claim 1, wherein the monitored brain signals comprise electroencephalogram signals.

7. The computer-implemented method of claim 1, comprising:

monitoring one or more biometrics of the user using one or more Internet of Things devices, and wherein said determining is based at least in part on the monitored one or more biometrics.

8. The computer-implemented method of claim 1, further comprising:

applying, by the at least one processor, a second encoding scheme to the removed brain signals, wherein the second encoding scheme results in a meaningless representation of the removed brain signals; and storing the encoded brain signals in a the storage system.

9. The computer-implemented method of claim 8, wherein the second encoding scheme comprises a randomized encoding scheme.

10. A computer program product comprising a computer readable storage medium having program instructions embodied therewith, the program instructions executable by a computing device to cause the computing device to perform at least:

presenting, by at least one processor of a brain sensing computing platform, a user with learning content;

monitoring, by the at least one processor of the brain sensing computing platform, brain signals of the user using a brain-computer interface associated with the brain sensing computing platform while the learning content is being presented to the user;

filtering, by the at least one processor of the brain sensing computing platform, the monitored brain signals to identify brain signals associated with a confusion state of the user, wherein the filtering removes one or more of the monitored brain signals based at least in part on one or more mappings between previously monitored brain signals of the user and one or more emotional states;

encoding, by the at least one processor of the brain sensing computing platform, the identified brain signals associated with the confusion state of the user using a first encoding scheme that is based at least in part on the one or more mappings corresponding to the user;

storing the encoded brain signals in a storage system associated with the brain sensing computing platform;

determining, by the at least one processor of the brain sensing computing platform based at least in part on the encoded brain signals stored in the storage system, that a confusion state of the user exceeds a personalized confusion threshold in regard to at least a part of the learning content; and in response to said determining, outputting, by the at least one processor of the brain sensing computing platform, information to assist the user in understanding the part of the learning content until the confusion state of the user falls below the personalized confusion threshold.

11. The computer program product of claim 10, wherein the program instructions executable by a computing device cause the computing device to perform:

generating, using at least one machine learning process, the one or more mappings between previously monitored brain signals of the user, wherein the one or more mappings further comprise at least one mapping between the previously monitored brain signal of the user and at least one of:

one or more words; one or more images; and one or more sounds.

12. The computer program product of claim 11, wherein the personalized confusion threshold is based at least in part on the one or more mappings.

13. The computer program product of claim 10, wherein the part of the learning content comprises one or more questions, and wherein the outputted information comprises further learning content related to one or more related concepts to guide the user to answer the one or more questions correctly.

14. The computer program product of claim 13, wherein the program instructions executable by a computing device cause the computing device to perform:

determining one or more characteristics associated with the user; and calculating a difficulty level of the one or more questions based at least in part on the one or more characteristics associated with the user and said monitoring.

15. The computer program product of claim 10, wherein the outputted information corresponds to at least one of: an image; a sound; a video; a hologram; and text, and wherein said outputting comprises determining a preferred modality of the user based at least in part on said monitoring and said determining.

16. The computer program product of claim 10, wherein the program instructions executable by a computing device cause the computing device to perform:

monitoring one or more biometrics of the user using one or more Internet of Things devices, and wherein said determining is based at least in part on the monitored one or more biometrics.

17. A system comprising:

one or more memories; and one or more processors, of a brain sensing computing platform, operably coupled to the one or more memories and configured to:

present, by at least one of the processors, a user with learning content;

monitor, by the at least one processor, brain signals of the user using a brain-computer interface associated with the brain sensing computing platform while the learning content is being presented to the user;

filter, by the at least one processor, the monitored brain signals to identify brain signals associated with a confusion state of the user, wherein the filtering removes one or more of the monitored brain signals based at least in part on one or more mappings between previously monitored brain signals of the user and one or more emotional states;

encode, by the at least one processor, the identified brain signals associated with the confusion state of the user using a first encoding scheme that is based at least in part on the one or more mappings corresponding to the user;

store the encoded brain signals in a storage system associated with the brain sensing computing platform;

determine, by the at least one processor based at least in part on the encoded brain signals stored in the storage system, that a confusion state of the user exceeds a personalized confusion threshold in regard to at least a part of the learning content; and in response to said determination, output, by the at least one processor, information to assist the user in understanding the part of the learning content until the confusion state of the user falls below the personalized confusion threshold.

18. A system comprising:

one or more memories; and one or more processors, of a brain sensing computing platform, operably coupled to the one or more memories and configured to:

present, by at least one of the processors, a user with learning content;

monitor, by the at least one processor brain signals of the user using a brain-computer interface while the learning content is being presented to the user, wherein the brain signals correspond to electrical activity sensed by the brain-computer interface;

identify, by the at least one processor, one or more confusion signals in the monitored brain signals of the user that indicate a level of confusion of the user, wherein the identifying comprises processing the monitored brain signals with a machine learning process that is trained to identify the one or more confusion signals based at least in part on one or more mappings between one or more external stimuli presented to the user and one or more previous brain signals of the user that were monitored while presenting the one or more external stimuli to the user;

filter, by the at least one processor, the monitored brain signals by removing brain signals that are not the identified one or more confusion signals;

encode, by the at least one processor, the identified one or more confusion signals using a first encoding scheme that is based at least in part on the one or more mappings;

store the encoded brain signals in a storage system associated with the brain sensing computing platform;

determine, by the at least one processor, based at least in part on the encoded brain signals stored in the storage system, that the level of confusion of the user exceeds a personalized confusion threshold in regard to at least a part of the learning content; and in response to said determination, output, by the at least one processor, information to assist the user in understanding the part of the learning content until the level of confusion of the user falls below the personalized confusion threshold.

19. The system of claim 18, wherein the information is output to the user in at least one of a plurality of modalities that is automatically selected based at least in part on the one or more mappings.

20. The system of claim 18, wherein the one or more processors are further configured to:

automatically update the one or more mappings based at least in part on additional brain signals of the user that are monitored in response to outputting the information.

* * * * *